US006855511B2

(12) United States Patent
Baker

(10) Patent No.: US 6,855,511 B2
(45) Date of Patent: Feb. 15, 2005

(54) FRUCTOSAMINE OXIDASE ASSAY: METHODS AND MATERIALS

(75) Inventor: John Richard Baker, Auckland (NZ)

(73) Assignee: Protemix Corporation Limited, Auckland (NZ)

(*) Notice: Subject to any disclaimer, the term of this patent is extended or adjusted under 35 U.S.C. 154(b) by 0 days.

(21) Appl. No.: 09/818,344

(22) Filed: Mar. 26, 2001

(65) Prior Publication Data

US 2002/0034775 A1 Mar. 21, 2002

(30) Foreign Application Priority Data

Sep. 25, 1998 (NZ) ................................................ 332085
Sep. 24, 1999 (NZ) .............................. PCT/NZ99/00160

(51) Int. Cl.$^7$ ............................................... C12Q 1/26

(52) U.S. Cl. ....................................................... 435/25

(58) Field of Search ........................................... 435/25

(56) References Cited

U.S. PATENT DOCUMENTS

| | | | |
|---|---|---|---|
| 4,374,829 A | 2/1983 | Harris et al. | |
| 4,410,541 A | 10/1983 | Kamimae et al. | |
| 4,758,583 A | 7/1988 | Cerami et al. | |
| 4,866,090 A | 9/1989 | Hoffman et al. | |
| 4,952,568 A | 8/1990 | Sawai et al. | |
| 5,128,360 A | 7/1992 | Cerami et al. | |
| 5,246,970 A | 9/1993 | Williamson et al. | |
| 5,852,009 A | 12/1998 | Cerami et al. | |

FOREIGN PATENT DOCUMENTS

| | | |
|---|---|---|
| AU | 30918/89 A | 9/1989 |
| AU | 80936/94 A1 | 5/1995 |
| AU | 14470/95 A | 7/1995 |
| AU | 41349/96 A1 | 5/1996 |
| DE | 3 217 071 A1 | 11/1983 |
| EP | 0 426 066 A2 | 5/1991 |
| GB | 2 192 789 A | 1/1988 |
| GB | 2 192 790 A | 1/1988 |
| JP | 57-144215 A | 9/1982 |
| WO | WO 87/05505 A1 | 9/1987 |
| WO | WO 99/39712 A1 | 8/1999 |
| WO | WO 00/18392 A1 | 4/2000 |
| WO | WO 00/18891 A1 | 4/2000 |

OTHER PUBLICATIONS

Chemistry Abstracts Registry numbers 4429–04–3, 57–48–7, 1 854–25–7.*
American Diabetes Association. (1997). "Report of the Expert Committee on the Diagnosis and Classification of Diabetes Mellitus," *Diabetes Care* 20:1183–1197.
American Diabetes Association. (1998). "Economic Consequences of Diabetes Mellitus in the U.S. in 1997," *Diabetes Care* 21(2):296–309.
Barthelmebs, M. et al. (1990). "L–Dopa and Streptozotocin–Induced Diabetic Nephropathy in Rats," *American Journal of Hypertension* 3(6 Part 2):72S–74S.
Barthelmebs, M. et al. (1991). "Effects of Dopamine Prodrugs and Fenoldopam on Glomerular Hyperfiltration in Streptozotocin–Induced Diabetes in Rats" *Journal of Cardiovascular Pharmacology* 18(2):243 –253.
Barthelmebs, M. et al. (1995); "Pathophysiological Role of Dopamine in the Kidney: Effects in Diabetes Mellitus and after Contralateral Nephrectomey," *Hypertens. Res.* 18(Suppl. I):S131–S136.
Baynes, J.W. (1991). "Role of Oxidative Stress in Development of Complications in Diabetes," *Diabetes* 40:405–412.
Boiadzhieva,N. (1990). "The Effect of Doparninergic Pharmocological Agents on the Pancreatic Islet Apparatus in Rats,"*Eksp. Med. Morfol.* 29(3):20–26. (English abstract).
Borgstrom, L. et al. (1986). "Pharmacokinetics of N–Acetylcysteine in Man," *Eur. J. Clin. Pharmacol.* 31:217–222.
Chan, P.C. and Bielski, B.H.J. (1974). "Enzyme–catalyzed Free Radical Reactions with Nicotinamide Adenine Nucleotides," *J. Biol. Chem.* 249(4):1317–1319.
Chan, P.C. and Bieiski, B.H.J. (1980). "Glyceraldehyde–3–Phosphate Dehydrogenase–catalyzed Chain Oxidation of Reduced Nicotinamide Adenine Dinucleotide by Perhydroxyl Radicals," *J. Biol Chem.* 255(3):874–876.
Chaturvedi, N. et al. (1998). "Effect of Lisinopril on Progression of Retinopathy in Norniotensive People with Type 1 Diabetes," *The Lance* 351:28–31.
Deckert T. et al. (1978). "Prognosis of Diabetics with Diabetes Onset before the Age of Thirtyone," *Diabetologia* 14:363–370.
Dubois, R.S. et al. (1970). "Triethylene Tetramine Dihydrochloride in Wilson's Disease," *Lancet* 2(7676):775.
Duchin, K.L. et al. (1988). "Pharmacokinetics of Captopril in Healthy Subjects and in Patients with Cardiovascular Diseases," *Clin. Pharmacokinetics* 14:241–259.
Elstner, E.F. and Heupel, A. (1976). "Inhibition of Nitrite Formation from Hydroxylammonium–chloride: A Simple Assay for Superoxide Dismutase," *Anal. Biochem.* 70:616–620.
Epstein, O. and Sherlock, S. (1980). "Triethylene Tetramine Dihydrochloride Toxicity in Primary Biliary Cirrhosis," *Gastroenterology* 78(6):1442–1445.

(List continued on next page.)

*Primary Examiner*—Sandra E. Saucier
(74) *Attorney, Agent, or Firm*—Buchanan Ingersoll P.C.

(57) ABSTRACT

Methods whereby, by reference to fructosamine oxidase activity in blood plasma of a patient or patients, the risk of diabetes associated vascular complications can be assessed, candidate fructosamine oxidase inhibitors and/or antagonists can be identified or tested and the inhibition and/or antagonism of the fructosamine oxidase inhibition and/or antagonism of a patient can be assessed.

25 Claims, 3 Drawing Sheets

OTHER PUBLICATIONS

Executive Committee of the International Union of Biochemistry, ed. (1979). *Enzyme Nomenclature, Recommendations of the Nomenclature Committee of the International Union of Biochemistry*, Academic Press: London, pp. 19–22. (Table of Contents).

Gennaro, A.R. ed. (1990). *Remington's Pharmaceutical Sciences*. 18th edition. Mack Publishing Company: Easton, Pennsylvania, 5 pages.(Table of Contents).

Gerhardinger, C. et al. (1995). "Novel Degradation Pathway of Glycated Amino Acids into Free Frudtosamine by a Pseudomonas sp. Soil Strain Extract," *J. Biol. Chem.* 270(1):218–224.

Greenstock, C.L. and Ruddock, G.W. (1976). "Determination of Superoxide ($O_2$) Radical Anion Reaction Rates Using Pulse Radiolysis,"*Int. J. Radiat. Phys. Chem.* 8:367–369.

Halliwell, B. (1976). "An Attempt to Demonstrate a Reaction between Superoxide and Hydrogen Peroxide," *FEBS Left.* 72( 1):8–10.

Halliwell, B. and Gutteridge, J.M.C. (1989). "The Superoxide Theory of Oxygen Toxicity," in *Free Radicals in Biology and Medicine*. Clarendon Press: Oxford, pp. 136–176.

Haslam, R.H. et al. (1980). "Treatment of Wilson's Disease with TriethyleneTetramine Dihydrochloride," *Dev. Pharmacol. Ther.* 1(5):318–324.

Holdiness M.R. (1991). "Clinical Pharmacokinetics of N–Acetylcysteine," *Clin. Pharmacokinet.* 20(2):123–134.

Horiuchi, T. et al. (1989). "Purification and.Properties of Fructosyl–amino Acid Oxidase from Corynebacterium sp. 2–4–1," *Agric. Biol. Chem.* 53(1):103–110.

Ido, Y. et al. (1996). "Interactions between the Sorbitol Pathway, Non–enzymatic Glycation, and Diabetic Vascular Dysfunction," *Nephrol. Dial. Transplant.* 11(Suppl 5):72–75.

Karisson, K. and Markiund, S.L. (1987). "Heparin–induced Release of Extracellular Superoxide Dismutase to Human Blood Plasma," *Biochem. J.* 242:55–59.

Kashihara, N. et al. (1992). "Selective Decreased de novo Synthesis of Glomerular Proteoglycans under the Influence of Reactive Oxygen Species," *Proc. Natl. Acad. Sci. USA* 89:6309–6313.

Klein, R.et al. (1985). "Retinopathy in Young–Onset Diabetic Patients," *Diabetes Care* 8(4):311–315.

Kodama, H. et al. (1997). "Metabolism of Administered Triethylene Tetramine Dihydrochioride in Humans," *Life Sci.* 61(9):899–907.

Marklund, S.L. et al. (1982). "Superoxide Dismnutase in Extracellular Fluids,"*Clin. Chimica Acta* 126:41–51.

Mattock, M.B. Ct al. (1998). "Microalbuminuria and Coronary Heart Disease in NIDDM: An Incidence Study," *Diabetes* 47:1786–1792.

McCord, J.M. and Fridovich, I. (1969). "Superoxide Dismutase: An Enzymic Function for Erythrocuprein (Hemocuprein)," *J. Biol. Chem.* 244(22):6049–6055.

Misra, H.P. and Fridovich, I. (1972). "The Role of Superoxide Anion in the Autoxidation of Epinephrine and a Simple Assay for Superoxide Dismutae," *J. Biol. Chem.* 247(10):3170–3175.

Misra, H.P. and Fridovich, I. (1977). "Superoxide Dismutase: 'Positive' Spectrophotometric Assays," *Anal. Biochem.* 79:553–560.

Mizobuchi, N. et at. (1993). "Serum Superoxide Dismutase (SOD) Activity in Diabetes Mellitus," *Rinsho Byori* 41:673–678. (English abstract).

Mogensen, C.E. and Christensen, C.K. (1984). "Predicting Diabetic Nephropathy in Insulin–dependent Patients," *New. Eng. J. Med* 311(2):89–93.

Mogensen, C.E. et al. (1992). "Microalbuminuria in Non–Insulin–Dependent Diabetes," *Clin. Nephrol.* 38(suppl 1):S28–S38.

Morpurgo, L. et at. (1990). "The Role of Copper in Bovine Serum Amine Oxidase," *Biol Metals* 3:114–117.

Obach, R. et al. (1984). "The Pharmacokinetic Profile of Carbidopa in Dogs," *J. Pharm. Pharmacol.* 36:415–416.

Palcic, M.M. and Janes, S.M. (1995). "Spectrophotometric-.Detection of Topa Quinone," *Meth. Enzymol.* 258:34–38.

Pappert, E.J. et al. (1997). "The Stability of Carbidopa in Solution," *Movement Disorders* 12(4):608–623.

Picard, S. et al. (1996). "Minimally Oxidised LDL as Estimated by a New Method Increase in Plasma of Type 2 Diabetic Patients with Atherosclerosis of Nephropathy," *Diabetes and Metabolism* 22(1):25–30.

Robbins, S.L. et al. (1984). "The Kidney," in *Pathologic Basis of Disease*. $3^{rd}$ ed., W.B. Saunders Company: Philadelphia, pp. 991–1061.

Saeki,. H. et al. (1998). "Malignant Syndrome Associated with Disseminated Intravascular Coagulation and a High Level of Amylase in Serum, Followed by Diabetic Coma in an Elderly Patient with Parkinson's Disease during L–Dopa Therapy," *Nippon Ronen Igakkai Zasshi* 35(2):139–144. (English abstract).

Saxena, A.K. et al. (1996). "Purification and Characterization of a Membrane–bound Deglycating Enzyme (1–Deoxyfructosyl Alkyl Amino Acid Oxidiise, EC 1.5.3) from a Pseudomonas sp. Soil Strain," *J. Biol. Chem.* 271(51):32803–32809.

Smith, P.R. and Thornalley, P.J. (1992). "Mechanism of the Degradation of Non–Enzymatically Glycated Proteins under Physiological Conditions," *Eur. J. Biochem.* 210:729–739.

Smith, S.A. and Pogson, C.I. (1977). "Trytophan and the Control of Plasma Glucose Concentrations in the Rat," *Biochem. J.* 168(3):495–506.

Sone, H. et al. (1996). "Inhibition of Hereditary Hepatitis and Liver Tumor Development in Long–Evans Cinnamon Rats by the Copper–Chelating Agent Trientine Dihydrochloride," *Hepatology* 23(4):764–770.

Talseth, T (1976). "Studies on Hydralazine," *Eur. J. Clin. Pharmacol.* 10(6):395–401.

Talseth, T. (1977). "Kinetics of Hydralazine Elimination," *Clin. Pharm. Thera.* 21(6):715–720.

Tanabe, R. Ct al. (1996). "Uptake Mechanism of Trientine by Rat Intestinal Brush–border Membrane Vesicles," *J. Pharm. Pharmacol.* 48:517–521.

The Diabetes Control and Complications Trial Research Group. (1993). "The Effect of Intensive Treatment of Diabetes on the Development and Progression of Long–term Complications in Insulin–dependent Diabetes Mellitus," *N. Eng. J. Med.* 329(14):977–986.

UKPDS Study Organisation. (1998). "Intensive Blood–glucose Control with Sulphonylureas or Insulin Compared with Conventional Treatment and Risk of Complications in Patients with Type 2 Diabetes (UKPDS 33)," *Lancet* 352:837–853.

Vailly, B. et al. (1990). "Prevention of L–dopa of Early Renal Consequences of Diabetes Induced by Strepotozocin in Rats," *Arch. Mal Coeur Vaiss.* 83(8):1259–1262. (English abstract).

Walshe, J.M. (1973). "Copper Chelation in Patients with Wilson's Disease: A Comparison of Penicillamine and Triethylene Tetramine Dihydrochloride," *Q J. Med New Series,* XLII(167):441–452.

Walshe, J.M. (1982). "Treatment of Wilson's Disease with Trientine (Triethylene Tetramine) Dihydrochloride," *Lancet* 8273:643–647.

Witztum, J.L. (1993). "Role of Oxidised Low Density Lipoprotein in Atherogenesis," *Br. Heart J.* 69(Suppl):S12–S18.

Wolff, S.P. et al. (1991). "Protein Glycation and Oxidative Stress in Diabetes Mellitus and Ageing," *Free Rad. Riot. Med.* 10:339–352.

Wynn, J.E. et al. (1970). "The Toxicity and Pharmacodynamics of EGTA: Oral Administration to Rats and Comparisons with EDTA,"*Toxicol. Appl. Pharmacol.* 16:807–817.

Yücel, D. et al. (1998). "Increased Oxidative Stress in Dilated Cardiomyopathic Heart Failure," *Clin. Chem.* 44(1):148–154.

* cited by examiner

FRUCTOSAMINE OXIDASE ASSAY: METHODS AND MATERIALS

CROSS-REFERENCE TO RELATED APPLICATIONS

This application claims priority to PCT/NZ99/00160 which was filed on Sep. 24, 1999 and to New Zealand patent application 332085 which was filed on Sep. 25, 1998; both of which are hereby incorporated by reference in their entirety.

THE CURRENT INVENTION

The present invention relates to methods and materials for the assay of fructosamine oxidase enzyme in patients and particularly but not solely those predisposed to or with diabetes mellitus.

Diabetes mellitus is a common disease characterized by serious long-term vascular complications. Diabetic individuals have a 25-fold increase in the risk of blindness, a 20-fold increase in the risk of renal failure, a 20-fold increase in the risk of amputation as a result of gangrene, and a 2- to 6-fold increased risk of coronary artery disease and ischemic brain damage. See, Klein R, Klein B, Davis M, DeMets D. *Diabetes Care* 8:311–5 (1985). Almost half those diagnosed as diabetic before the age of 31 years die before they reach 50 years largely as a result of cardiovascular or renal complications, often with many years of crippling and debilitating disease beforehand. See, Deckert T, Poulsen J, Larsen M. *Diabetologia* 14:363–70 (1978).

Elevated blood glucose levels are now regarded as causative of diabetic complications based on results of the Diabetes Complications and Control Trial (DCCT) and the United Kingdom Prospective Diabetes Study (UKPDS). See, The Diabetes Control and Complications Trial Research Group. *N Eng J. Med.* 379:977–85 (1993) and *Lancet* 352:837–53 (1998). The DCCT and the UKPDS have both demonstrated that the development of complications of diabetes are related with degree of hyperglycemia and the long-term outcome may be ameliorated by rigourous treatment. After controlling for currant $HbA_{1c}$ levels, the development of micro vascular complications in DCCT patients was strongly correlated with the degree of nonenzymatic glycation of structural proteins such as skin collagen, but not with advanced glycation end product (AGE) markers such as pentosidine, carboxymethylysine, and tissue fluorescence (V Monnier —personal communication). These findings imply that the nonenzymatic glycation of tissue proteins has greater pathophysiological importance than AGE formation.

Many of the features of diabetic vascular disease may also be attributed to oxidative stress, defined as an increase in the steady-state level of reactive oxygen or oxygen radicals in a biological system See, Baynes JW. *Diabetes* 40;405–12 (1991). For example, superoxide anions increase intracellular calcium which modulates the activity of nitric oxide synthase in the endothelium. Nitric oxide is a potent vasodilator and it has been implicated in the vascular dysfunction of early diabetes See, Ido Y, Kilo C, Williamson JR. *Nephrol Dial Transplant* 11 Suppl 5:72–5 (1996). Reactive oxygen species precipitate a drastic dose-dependent decrease in de novo synthesis of heparin sulfate proteoglycans leading to a reduction in anionic sites on the basement membrane and to an increased permeability to positively charged proteins such as albumin See, Kashira N, Watanabe Y, Makin H, Wallner EI, & Kanwar YS. *Proc Natl Acad Sci USA* 89:6309–13 (1992). Such leaky capillaries manifest clinically as background retinopathy and microalbumiuria. Microalbumiuria, in turn, is a recognized risk factor both for diabetic nephropathy in IDDM and for coronary artery disease and sudden death in elderly NIDDM See, Mogensen CE, Christensen CK. *N Eng J Med* 311;89–93 (1984) & Mogensen CE, Damsgaard EM, Froland A, et al *Clin Nephrol* 38 (suppl 1);s28–39 (1992).

Once natural anti-oxidant defenses are exceeded, there is the potential for hydroxyl radical generation from superoxide via a copper catalyzed Haber-Weiss reaction See, Halliwell B & Gutteridge JMC "Free radicals in Biology and Medicine" Clarendon Press, Oxford (pp. 136–76 1989). Hydroxyl radicals are extremely reactive species that cause serious site-specific damage.

Oxygen radicals have also been implicated in the oxidative modification of low density lipoprotein (LDL) See, Witztum JL. *Br Heart J* 69; S12–S18 (1993). Oxidized LDL is a specific risk factor for atherosclerosis, binding with a scavenger receptor on tissue macrophages leading to the formation of foam cells and to cholesteryl ester accumulation in the internal fatty streak, a feature of atheromatous plaque formation.

To date, the source of the oxidative stress in diabetes has not been identified. I have isolated a novel extracellular enzyme which catalyses the elimination of fructosamines from glycated protein. The existence of this enzyme has not previously been recognized in the world literature. The reaction is important because fructosamine is the precursor of all the Maillard products. Based on its high specificity for glycated protein substrates and its use of oxygen as acceptor, the enzyme may be classified as fructosamine oxidase 1.5.3. See, Enzyme nomenclature, Recommendations of the Nomenclature Committee of the International Union of Biochemistry, Academic Press, London pp. 19–22, (1979). Fructosamine oxidase is a metalloenzyme with copper and quinone cofactors. Reaction products are free unglycated protein, α-dicarbonyl sugar, and superoxide (FIG. 1).

SUMMARY OF THE INVENTION

The existence of the fructosamine oxidase enzyme has not previously been recognized in the world literature. This is a novel enzyme. The present invention relates to methods of monitoring fructosamine oxidase inhibition and/or antagonism of patients, methods for testing or identifying fructosamine oxidase inhibitors, methods of screening patients to determine patients at risk to vascular (particularly microvascular) damage and methods of identifying those individuals who will benefit by treatment with fructosamine oxidase inhibitors and/or antagonists, methods of determining fructosamine oxidase levels in a mammal, methods of determining blood plasma fructosamine oxidase levels in a diabetic individual or a suspected individual, methods of assaying blood serum or blood plasma in vitro for fructosamine oxidase and to related methods and procedures.

In one aspect the invention consists in a method of determining fructosamine oxidase activity in blood plasma of mammalian patients or a mammalian patient to determine patients or a patient at risk to vascular damage, which method comprises determining the levels of fructosamine oxidase and/or the superoxide reaction product of fructosamine oxidase and/or any other oxygen free radical product of fructosamine oxidase in the population of patients and making the determination dependant upon such levels.

Preferably the patients are humans suffering from or predisposed to diabetes.

Preferably said fructosamine oxidase activity is measured in blood taken from each patient.

Preferably the measurement conducted in vitro is of the superoxide reaction product or any other oxygen free radical product of fructosamine oxidase.

Preferably at risk patients are or an at risk patient is then treated inter alia to inhibit and/or to antagonize fructosamine oxidase.

Accordingly, in another aspect the present invention consists in a method of screening mammalian patients (preferably humans suffering from or predisposed to diabetes) to determine patients at risk to vascular (particularly microvascular) damage, which method comprises determining the levels of fructosamine oxidase and/or the superoxide reaction product (or any other oxygen free radical product) of fructosamine oxidase in the population of patients and making the determination dependant upon such levels.

Preferably said screening is of blood taken from each patient.

Preferably the measurement conducted in vitro is of the superoxide reaction product (or any other oxygen free radical product) of fructosamine oxidase.

Preferably at risk patients are then treated inter alia to inhibit and/or to antagonize the fructosamine oxidase.

Preferably the procedure is substantially as hereinafter described.

In still a further aspect, the present invention consists in a method of identifying those individuals who will benefit by treatment with fructosamine oxidase inhibitors and/or antagonists, which method comprises testing an individual or a group of individuals for fructosamine oxidase in their blood directly or by reference to the superoxide reaction product (or any other oxygen free radical product) of fructosamine oxidase.

Preferably at risk patients are then treated inter alia to inhibit and/or to antagonize the fructosamine oxidase.

Preferably the procedure is substantially as hereinafter described.

In still a further aspect, the present invention consists in a method of monitoring fructosamine oxidase inhibition and/or antagonism of a patient which comprises or includes testing (directly or indirectly) the fructosamine oxidase level of such patient.

Preferably such testing is by reference to the superoxide reaction product (or any other oxygen free radical product of fructosamine oxidase) in the blood of the patient.

Preferably each of the methods involves a determination of a particular level attributed to fructosamine oxidase and/or the reaction products referred to in comparison to such level or levels of a patient or patients (as the case may be) who is or are not at risk to such vascular damage, or will not benefit by treatment with fructosamine oxidase inhibitors and/or antagonists or have no need for fructosamine oxidase inhibition and/or antagonism.

In another aspect the invention consists in a method of testing and/or identifying fructosamine oxidase inhibitors or a fructosamine oxidase inhibitor which comprises measuring the effect a candidate substance has or candidate substances have on one or more of the quinone co-factor, or the copper co-factor of fructosamine oxidase.

In yet another aspect the invention consists in a method of identifying a candidate substance for trial for the amelioration of diabetes induced vascular damage in a mammal which comprises testing such a substance for fructosamine oxidase inhibition and/or antagonism and choosing to trial the substance where (i) it has a specificity for such an enzyme or its co-factors and (ii) it has an effectiveness for such inhibition and/or antagonism at dosage levels not known to be toxic or contraindicated in such a mammal.

In still a further aspect the present invention consists in the measurement in vitro of the superoxide reaction product (and/or any other oxygen free radical product) of fructosamine oxidase in the blood of a mammal by exploiting its reductant properties or its oxidant properties or by enzymatic means.

In one preferred form said measurement procedure involves (preferably at a pH 7 to 8 (most preferably at pH greater than 7.5)) the disabling of the superoxide scavenging mechanism (such as superoxide dismutase) (SOD) [e.g. using potassium cyanide or (more preferably) by pretreatment with antihuman CuZn SOD antisera] and then exposure [e.g. by addition] to a suitable fructosamine oxidase substrate [e.g. glycated bovine serum albumin modified to eliminate copper chelating activity which might disable the fructosamine oxidase].

Preferably the measurement following from the preferred procedure described involves a consideration [e.g. measurement] of an absorbance change, chemiluminescent change, or some other characterizing change in an indicator of the modified sample.

In still a further aspect the present invention consists in a method of determining the fructosamine oxidase levels in a mammal (human or non-human) which at least includes procedures as previously set forth.

In still a further aspect the present invention consists in a method of determining blood plasma fructosamine oxidase levels in a diabetic individual or a suspected diabetic individual which comprises at least steps of a method as previously set forth.

In still a further aspect the present invention consists in a method of assaying blood serum or blood plasma in vitro (directly and/or indirectly) for fructosamine oxidase which involves at least one or more of the steps or procedures hereinbefore described and/or hereinafter described.

In still a further aspect the present invention consists in a blood serum or blood plasma sample of a patient in which the superoxide scavenging mechanisms therein have been disabled and the pH is in the range from 7 to 8.

Preferably said sample also includes or has been modified by exposure to a suitable fructosamine oxidase substrate.

Preferably said fructosamine oxidase substrate is glycated bovine serum albumin modified to eliminate copper chelating activity which might disable fructosamine oxidase.

In still a further aspect the present invention consists in the use of a sample in accordance with the present invention for the purpose of any of the methods previously set forth.

The attention of the reader is drawn to my simultaneously filed PCT Application (claiming New Zealand priorities from NZ 332084, NZ 332079 and NZ 334471) in which there are disclosed a variety of procedures, methods, pharmaceutical compositions, dosage units etc. involving the use of fructosamine oxidase inhibition and/or antagonism in order to reduce vascular (preferably microvascular) damage to patients (particularly although not solely diabetic or suspected diabetic patients).

Preferably any such inhibitor or antagonist is selected from the groups (i) copper chelating agents (e.g., triethylenetetramine dihydrochloride, penicillamine, sar, diamsar, ethylenediamine tetraacetic acid, o-phenanthroline and histidine)

(ii) substrate analogues (e.g., N-acetylcysteine, captropril and enalapril).
(iii) hydrazine compounds ((e.g., diaminoguanidine, hydralazine and carbidopa).

As used herein including the appended claims the term "and/or" means "and" or "or".

The full content of the simultaneously filed PCT International patent specification is hereby included by way of cross reference.

DETAILED DESCRIPTION OF THE INVENTION (i) Assay Principle

Figure 1:
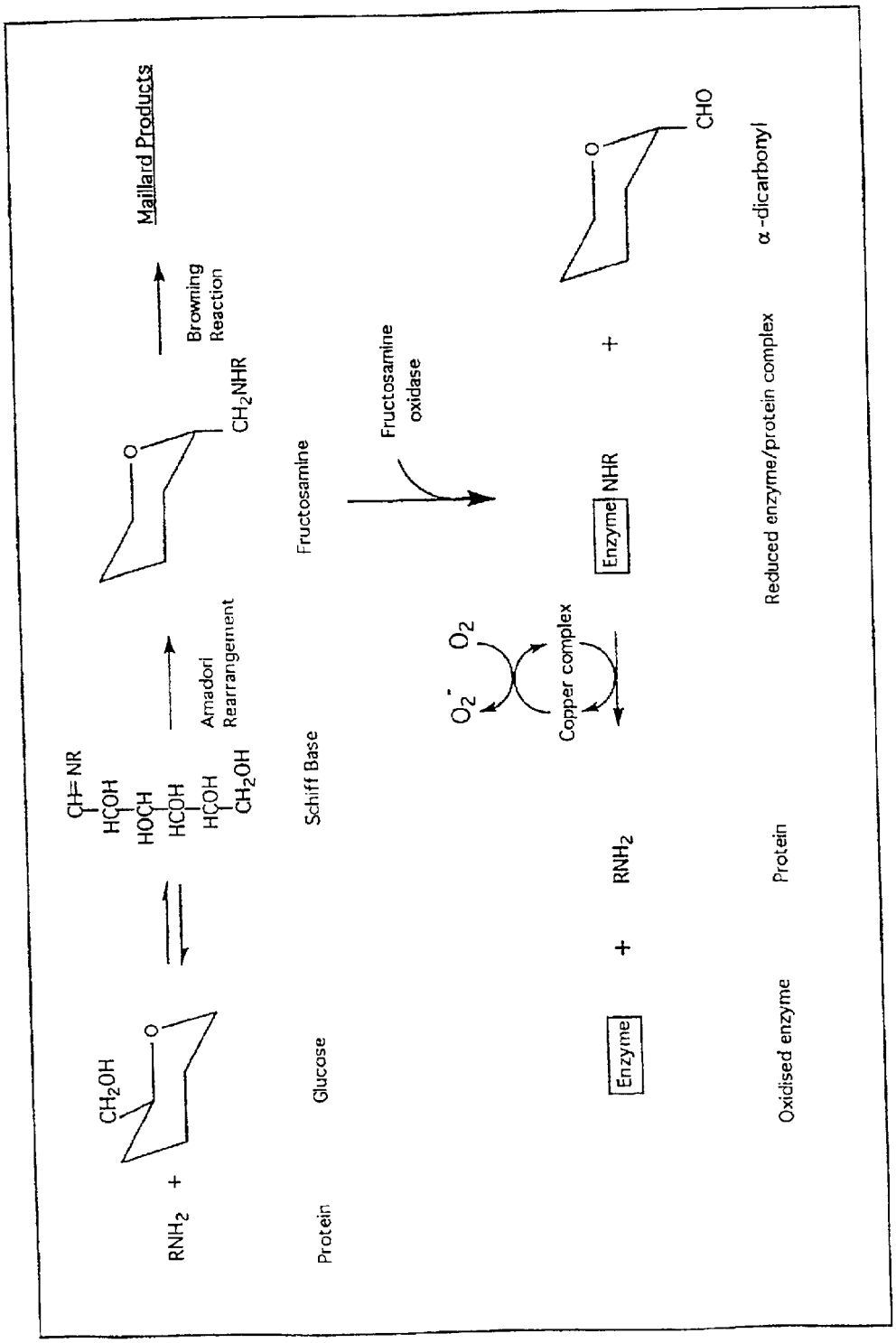
FIG. 1 shows a detailed reaction mechanism for the formation of fructosamine and Maillard products from glucose and protein. Fructosamine oxidase degrades fructosamine by a two-step reaction with initial release of an α-dicarbonyl sugar and subsequent oxidation of the enzyme/protein complex to release free unglycated protein. The reduced copper cofactor is oxidized in vivo by molecular oxygen and the oxidation product is superoxide.

*Fructosamine oxidase* catalyses the degradation of fructosamine(s) with concurrent reduction of molecular oxygen yielding a superoxide reaction product (FIG. 1). Superoxide is unstable in aqueous solution with spontaneous dismutation to hydrogen peroxide and oxygen. The dismutation reaction is strongly pH dependent with maximal reactivity in acidic solutions and reducing reactivity in alkaline solution. Therefore, enzyme activity is best determined at pH values 7.0–8.0 and preferably about pH 7.5 where superoxide is more stable using one of the assay compounds listed in Table 1.

TABLE 1

| Assay compound | Assay pH | Type of Reaction | Reference |
|---|---|---|---|
| Ferricytochrome c | 7.8 | Reduction | McCord J & Fridovich I. J Biol Chem 244;6087-93 (1969) |
| Nitroblue tetrazolium | 7.8 | Reduction | Halliwell B FEBS Lett 72;8 (1976) |
| Dichlorphenol indophenol | 7.0 | Reduction | Greenstock CL & Ruddock GW. Int J Radiat Phys Chem 8;367 (1976) |
| Epinephrine | 7.8 | Oxidation | Misra HP & Fridovich I J Biol Chem 247;3170-5 (1972) |
| Hydroxylamine | 7.8 | Oxidation | Elstner EF, Heupel A. Anal Biochem 70;616-20 (1976) |
| Peroxidase | 7.8 | Enzymatic | Misra HP, Fridovich I Anal Biochem 79;553-60 (1977) |
| NADH...LDG | 7.0 | Enzymatic | Chan PC & Bielski BHJ. J Biol Chem 249;1317-9 (1974) |
| NADH...GDH | 7.2 | Enzymatic | Chan PC & Bielski BHJ. J Biol Chem 255;874-6 (1980) |

(ii) Interference

Because superoxide is potentially a noxious substance, superoxide degrading enzyme, superoxide dismutase (SOD), is elaborated in plasma as a physiological response to increasing superoxide concentrations. Compared with healthy non-diabetic individuals, SOD levels are significantly elevated in the plasma of patients with diabetes mellitus and particularly amongst those patients with microvascular disease such as diabetic nephropathy and diabetic retinopathy. See, Mizobuchi N, Nakata H, Horimi T, Takahashi I. *Rinsho Byori* 41;673–8 (1993). The major SOD isoenzyme in extracellular fluids like plasma is extracellular SOD which is a tetrameric glycoprotein that contains four copper atoms and four zinc atoms. See, Karlsson K & Marklund SL *Biochem J* 242;55–9 (1987). Unless it is disabled, such SOD activity will cause significant interference in any blood plasma assay based on the detection systems listed in Table 1.

Almost all of the SOD activity of human plasma is sensitive to inhibition with millimolar concentrations of potassium cyanide, sodium azide or sodium fluoride. Alternatively, SOD activity of plasma may be eliminated by pre-treatment of the plasma sample with anti-human CuZn SOD antisera. See, Marklund SL, Holme E, Hellner L *Clin Chem Acta* 126;41–51 (1982).

(iii) Procedure

*Fructosamine oxidase* activity may be measured using the redox-active color reagent, ferricytochrome c, which is readily reduced by superoxide to form ferrocytochrome c with a characteristic increase in absorbance at 550 nM ($E_{550}$ 22.1 $mM^{-1}.cm^{-1}$). The reagent is 50 mM TES buffer pH 7.4 containing 10 μM cytochrome c (Sigma), and 50 μM and 50 μM fructosamine as glycated bovine serum albumin. The parameters for performance of the assay in a Cobas Bio (Roche) automated analyzer are as shown in Table 2.

TABLE 2

PARAMETER LISTING

| 1 | UNITS | U/L |
|---|---|---|
| 2 | CALCULATION FACTOR | 473.9 |
| 3 | STANDARD 1 CONCENTRATION | 0 |
| 4 | STANDARD 2 CONCENTRATION | 0 |
| 5 | STANDARD 3 CONCENTRATION | 0 |
| 6 | LIMIT | 0 |
| 7 | TEMPERATURE [DEG.C] | 30.0 |
| 8 | TYPE OF ANALYSIS | 6 |
| 9 | WAVELENGTH [NM] | 550 |
| 10 | SAMPLE VOLUME [UL] | 5 |
| 11 | DILUENT VOLUME [UL] | 45 |
| 12 | REAGENT VOLUME [UL] | 200 |
| 13 | INCUBATION TIME [SEC] | 300 |
| 14 | START REAGENT VOLUME [UL] | 25 |
| 15 | TIME OF FIRST READING [SEC] | 0.5 |
| 16 | TIME INTERVAL [SEC] | 300 |
| 17 | NUMBER OF READINGS | 2 |
| 18 | BLANKING MODE | 1 |
| 19 | PRINTOUT MODE | 1 |

One unit of enzyme was defined as the amount which reduced 1 μmol/minute of cytochrome c in solution under the above assay conditions. The calculation factor is determined from the molar absorptivity for ferrocytochrome c ($E_{550nm}$) according to the formula:

$$U/L(\mu mol.min^{-1}.L^{-1}) = TV \times 10^3 / \epsilon_{550nm} \times SV$$

where

TV=total reaction volume

SV=sample volume

(iv) Materials

Glycated bovine serum albumin substrate was prepared as follows:

(a) Bovine serum albumin (BSA) (Sigma) was reduced with sodium borohydride to eliminate protein hydroperoxides. BSA (60 g/L) was dissolved in 0.145M NaCl, pH was adjusted to 9.0 with molar NaOH, sodium borohydride (200 mmol/L) was added, and the solution was stirred gently at room temperature for 24 hours. Excess sodium borohydride was discharged with glacial acetic acid and the solution was dialyzed exhaustively against 0.145M NaCl at 4° C.

(b) Borohydride-reduced BSA was glycated by mixing protein solution with an equal volume 0.4M $Na_2PO_4$ buffer pH 7.4 containing 50 mM glucose and 0.02% sodium azide and incubating at 37° C. for 7 days. Excess glucose was removed by exhaustive dialysis against 0.145 M NaCl.

(c) Glycated BSA (GBSA) was acetylated by adding 0.2 M iodoacetic acid, adjusting pH to 6.8, and incubating at room temperature for 24 hours. Excess iodoacetate was removed by exhaustive dialysis against 0.145 M NaCl.

(d) Remaining copper binding sites on gBSA were saturated by dialyzing against 0.145 M NaCl containing 100 $\mu$M copper sulfate. Excess copper was removed by exhaustive dialysis against 0.145 M NaCl.

(e) Degree of glycation of GBSA substrate was determined by fructosamine assay (Hoffmann La-Roche).

(v) Substrate Specificity

The specificity of the assay for reactive oxygen species was tested by measuring degree of inhibition of ferricytochrome c reduction after adding the following oxygen free radical scavengers to the reaction mixture: (a) Superoxide dismutase to selectively remove superoxide; (b) catalase to selectively remove hydrogen peroxide; & (iii) mannitol to scavenge hydroxyl radicals. Results are shown in Table 3.

TABLE 3

| Free radical scavenger | Enzyme activity* (U/L) | Significance (P) |
|---|---|---|
| Control | 15.34 ± 0.16 | — |
| superoxide dismutase (20 kU/L) | 9.99 ± 0.03 | <0.0001 |
| catalase (1000 kU/L) | 12.23 ± 0.03 | <0.0001 |
| superoxide dismutase + catalase | 6.78 ± 0.12 | <0.0001 |
| mannitol (50 mmol/L) | 14.96 ± 0.19 | 0.0421 |

*determined with free radical scavenger added to the reagent. Results imply that the assay reaction is measuring both superoxide and hydroxyl radicals formed from the reaction of superoxide with hydrogen peroxide.

5 (v) Specificity

Cytochrome c is a non-specific reductant and other reducing substances in sera or anticoagulants added to the blood sample at specimen collection may interfere in the assay as shown in Table 4.

TABLE 4

| Additive | Activity compared with control (%) |
|---|---|
| Control | 100 |
| Heparin (1000 U/L) | 24.4 |
| EDTA (100 $\mu$M) | 26.3 |

*Human fructosamine oxidase analyzed with and without (control) additive in the reagent

(vi) Comparison with Fructosamine Concentrations

Figure 2:
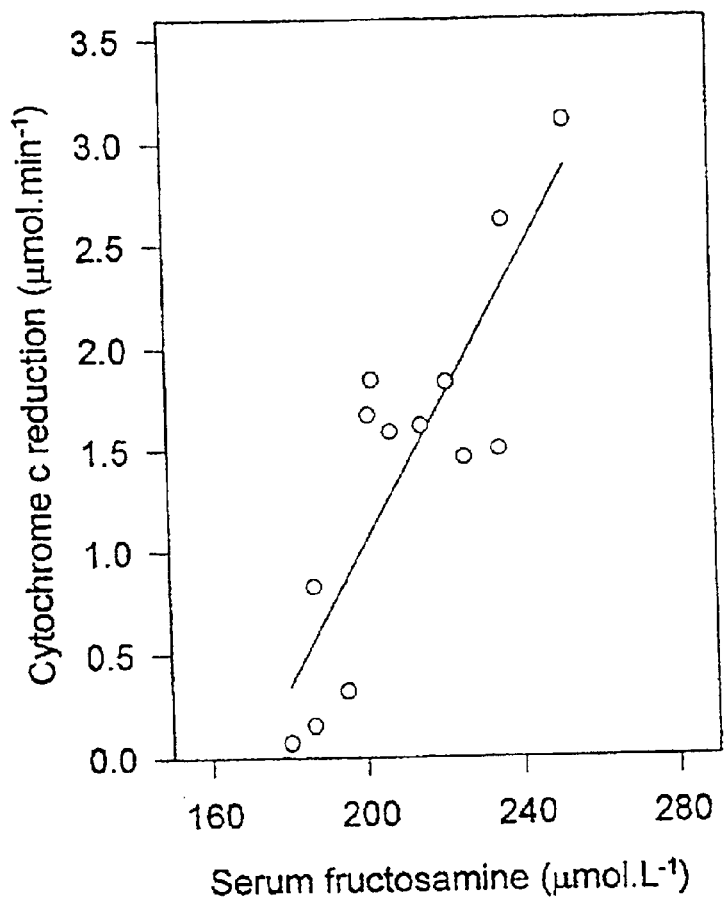
FIG. 2 shows the relationship between fructosamine oxidase measurements and plasma fructosamine. Linear regression equation (y=0.0349x−5.9589; $r^2$=0.7455).

Fructosamine oxidase activity was measured in non-diabetic sera and results were compared with serum fructosamine concentrations FIG. 2.

(vii) Identifying *Fructosamine oxidase* Inhibitors

Figure 3:
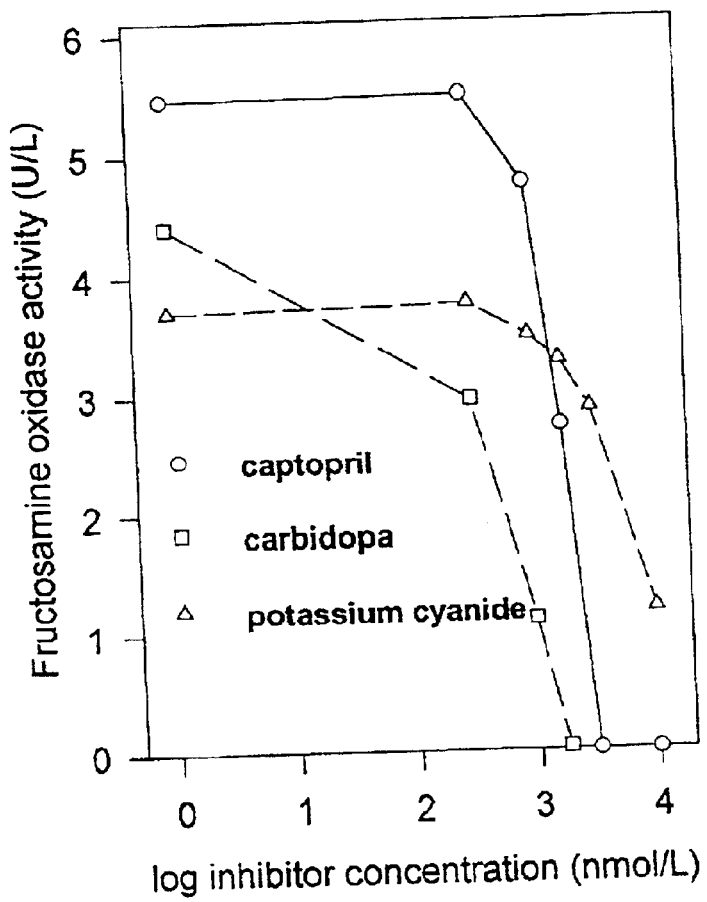
FIG. 3 shows the effect of fructosamine oxidase inhibitors on enzyme activity in human blood plasma. The three inhibitors are selected, merely by way of example, from the three classes of compounds which inhibit the enzyme (i.e. captopril is a substrate analogue, carbidopa is a hydrazine compound, and potassium cyanide is a copper chelator).

An important application of the current activity assay is as a means to identify potential *fructosamine oxidase* antagonists and inhibitors. Fructosamine oxidase inhibitors may be hydrazine compounds which bind and block the quinone co-factor, copper chelators which bind and block the copper co-factor, or substrate analogues which mimic the normal substrate of the enzyme. Micromolar amounts of candidate substance are added to the reaction mixture, and the decrease in *fructosamine oxidase* activity of a human plasma sample is measured. The inhibitory potential of carbidopa, (hydrazine compound), potassium cyanide (copper chelator), and captopril (substrate analogue) are demonstrated in FIG. 3.

The effectiveness of an enzyme inhibitor is usually expressed by a velocity constant (K) which determines the fraction of the enzyme inhibited in a given period of time by a certain concentration of inhibitor. The specificity of the inhibitor for the active center of the enzyme is indicated by the concentration of inhibitor causing 50% inactivation of the enzyme ($IC_{50}$). Results of this in vitro assay would suggest that, at 1 pM inhibitor concentration, the most effective enzyme inhibitor is carbidopa, (K=15% per minute) followed by captopril (K=2.6% per minute) followed potassium cyanide (K=1.2% per minute). Carbidopa, also shows the greatest specificity for the active center of *fructosamine oxidase* ($IC_{50}$=0.50 $\mu$M) compared with captopril ($IC_{50}$=0.83 $\mu$M) and potassium cyanide ($IC_{50}$=6.36 $\mu$M).

What is claimed is:

1. A method of determining a level of fructosamine oxidase activity in a sample comprising measuring the conversion of a substrate glycated protein to a product catalyzed by fructosamine oxidase, wherein a superoxide scavenging mechanism is disabled in said method.

2. The method of claim 1 wherein the conversion is measured by determining a level of superoxide reaction product.

3. The method of claim 1 wherein the conversion is measured by determining a level of oxygen free radical product.

4. The method of claim 1 wherein a superoxide scavenging mechanism is disabled prior to exposure to a substrate.

5. The method of claim 4 wherein the substrate is glycated bovine serum albumin.

6. The method of claim 5 wherein the glycated bovine serum albumin is modified to eliminate copper chelating activity.

7. The method of claim 1 wherein measurements are made at a pH of 7 to 8.

8. The method of claim 1 wherein measurements are made at a pH greater than 7.5.

9. The method of claim 1 wherein the sample is selected from the group consisting of blood, plasma, and serum.

10. The method of claim 1 wherein the measurement of conversion of a substrate to a product by fructosamine oxidase is conducted on a sample from a human subject.

11. The method of claim 10 wherein the human subject is known to be, or suspected of, suffering from diabetes mellitus.

12. The method of claim 11 further comprising determining whether the level of fructosamine oxidase activity in the sample is in a normal range.

13. A method of determining a level of fructosamine oxidase activity in a sample comprising measuring conversion of a substrate to a product catalyzed by a mammalian fructosamine oxidase.

14. A method of determining a level of fructosamine oxidase activity in a sample comprising measuring the conversion of a substrate to a product catalyzed by fructosamine oxidase, wherein the sample is from a human subject.

15. The method of claim 13 or 14 wherein the conversion is measured by determining a level of superoxide reaction product.

16. The method of claim 13 or 14 wherein the conversion is measured by determining a level of oxygen free radical product.

17. The method of claim 13 or 14 wherein measurements are made at a pH of from about 7 to about 8.

18. The method of claim 13 or 14 wherein measurements are made at a pH greater than about 7.5.

19. The method of claim 13 or 14 wherein a superoxide scavenging mechanism is disabled in said method.

20. The method of claim 19 wherein a superoxide scavenging mechanism is disabled prior to exposure to a substrate.

21. The method of claim 20 wherein the substrate is glycated bovine serum albumin.

22. The method of claim 21 wherein the glycated bovine serum albumin is modified to eliminate copper chelating activity.

23. The method of claim 14 wherein the sample is selected from the group consisting of blood, plasma, and serum.

24. The method of claim 14 wherein the human subject is known to be, or suspected of, suffering from diabetes mellitus.

25. The method of claim 24 further comprising determining whether the level of fructosamine oxidase activity in the sample is in a normal range.

* * * * *